(12) United States Patent
Stenzel et al.

(10) Patent No.: US 8,597,425 B2
(45) Date of Patent: *Dec. 3, 2013

(54) HIGHLY DISPERSIBLE SILICA FOR USING IN RUBBER

(75) Inventors: Oleg Stenzel, Köln (DE); Anke Blume, Weilerswist (DE); Hans-Detlef Luginsland, Hoboken, NJ (US); Stefan Uhrlandt, Belle Mead, NJ (US); André Wehmeier, Hürth (DE)

(73) Assignee: Evonik Degussa GmbH, Essen (DE)

( * ) Notice: Subject to any disclaimer, the term of this patent is extended or adjusted under 35 U.S.C. 154(b) by 1565 days.

This patent is subject to a terminal disclaimer.

(21) Appl. No.: 10/542,763

(22) PCT Filed: Jan. 8, 2004

(86) PCT No.: PCT/EP2004/050005

§ 371 (c)(1),
(2), (4) Date: Jan. 17, 2006

(87) PCT Pub. No.: WO2004/065299

PCT Pub. Date: Aug. 5, 2004

(65) Prior Publication Data

US 2006/0165581 A1    Jul. 27, 2006

(30) Foreign Application Priority Data

Jan. 22, 2003  (DE) .................. 103 02 300
Dec. 13, 2003  (DE) .................. 103 58 449

(51) Int. Cl.
    *C01B 33/18*     (2006.01)
(52) U.S. Cl.
    USPC .................. 106/481; 423/335; 423/339
(58) Field of Classification Search
    USPC .......... 106/482, 486, 490; 423/338, 335, 339; 524/492
    See application file for complete search history.

(56) References Cited

U.S. PATENT DOCUMENTS

| | | | |
|---|---|---|---|
| 5,846,506 A * | 12/1998 | Esch et al. ................ | 423/338 |
| 5,935,543 A * | 8/1999 | Boyer et al. ............... | 423/339 |
| 6,077,466 A | 6/2000 | Türk et al. | |
| 6,180,076 B1 * | 1/2001 | Uhrlandt et al. ........... | 423/335 |
| 6,268,424 B1 | 7/2001 | Blume et al. | |
| 6,613,309 B2 | 9/2003 | Uhrlandt et al. | |
| 6,624,230 B2 | 9/2003 | Luginsland | |
| 6,702,887 B2 | 3/2004 | Uhrlandt et al. | |
| 6,846,865 B2 | 1/2005 | Panz et al. | |
| 6,849,754 B2 | 2/2005 | Deschler et al. | |
| 6,893,495 B2 | 5/2005 | Korth et al. | |
| 6,899,951 B2 | 5/2005 | Panz et al. | |
| 6,984,683 B2 | 1/2006 | Luginsland et al. | |
| 7,022,375 B2 | 4/2006 | Schachtely et al. | |
| 7,074,457 B2 | 7/2006 | Panz et al. | |
| 7,208,038 B2 | 4/2007 | Korth et al. | |
| 7,220,449 B2 | 5/2007 | Schachtely et al. | |
| 7,566,433 B2 | 7/2009 | Stenzel et al. | |
| 7,608,234 B2 | 10/2009 | Stenzel et al. | |
| 2002/0022693 A1 * | 2/2002 | Luginsland ............... | 525/100 |
| 2003/0059380 A1 | 3/2003 | Uhrlandt et al. | |
| 2003/0082090 A1 * | 5/2003 | Blume et al. .............. | 423/335 |
| 2003/0162881 A1 * | 8/2003 | Panz et al. ................. | 524/493 |
| 2005/0187334 A1 | 8/2005 | Blume et al. | |

FOREIGN PATENT DOCUMENTS

| | | |
|---|---|---|
| EP | 0 754 650 | 1/1997 |
| EP | 0 755 899 | 1/1997 |
| EP | 0 901 986 | 3/1999 |
| EP | 0 983 966 | 3/2000 |
| JP | 09-118516 | 5/1977 |
| JP | 11-157826 | 6/1999 |
| JP | 2000-072434 | 3/2000 |
| WO | 03/106339 | 12/2003 |

OTHER PUBLICATIONS

U.S. Appl. No. 10/522,672, filed Jan. 28, 2005, Stenzel, et al.
U.S. Appl. No. 10/516,308, filed Dec. 10, 2004, Uhrlandt, et al.
U.S. Appl. No. 10/523,414, filed Feb. 3, 2005, Stenzel, et al.
U.S. Appl. No. 10/523,029, filed Feb. 2, 2005, Stenzel, et al.
U.S. Appl. No. 10/542,850, filed Jul. 21, 2005, Luginsland, et al.

* cited by examiner

*Primary Examiner* — Pegah Parvini
(74) *Attorney, Agent, or Firm* — Oblon, Spivak, McClelland, Maier & Neustadt, L.L.P.

(57) ABSTRACT

The present invention relates to highly disperse precipitated silicas which exhibit an extremely high level of reinforcement of rubber vulcanizates, to a process for their preparation, and to their use as filler for rubber mixtures.

20 Claims, No Drawings

HIGHLY DISPERSIBLE SILICA FOR USING IN RUBBER

The present invention relates to highly disperse precipitated silicas which exhibit an extremely high level of reinforcement of rubber vulcanizates and advantages in vulcanization time, to a process for their preparation, and to their use as filler for rubber mixtures.

The use of precipitated silicas in elastomer mixtures, such as tire tread mixtures, has been known for a long time (EP 0 501 227). There are stringent requirements relating to the use of silicas as a reinforcing filler in rubber mixtures, for example those used to produce pneumatic tires and technical rubber products. They have to have low density and have good capability for incorporation and dispersion in the rubber, and undergo chemical bonding to the rubber in association with a coupling reagent, preferably a bifunctional organosilicon compound, this reaction leading to the desired high level of reinforcement of the rubber mixture. The property of reinforcement can in particular be associated with high static stress values and a low abrasion value. The particle size, surface morphology, surface activity, and also the binding power of the coupling reagent, are of particularly decisive importance in relation to the reinforcing property of the silicas.

It is known that the properties of a silica are decisively determined by its preparation process. The properties are in particular affected by the conditions of precipitation. The person skilled in the art is aware of preparation processes for silicas with a very wide variety of precipitation conditions. For example, EP 0 937 755 describes precipitations at constant pH. DE 101 24 298 disclosed silicas which were precipitated at constant cation excess. DE 101 12 441 A1, EP 0 754 650, EP 0 755 899, and U.S. Pat. No. 4,001,379 described precipitations at constant alkali value (AV).

Silicas which were precipitated at constant AV are used as carrier materials, matting agents for paints, as battery separators, in toothpastes, or as flocculation agents. There have hitherto been no known silicas which were precipitated at constant AV and are suitable for applications in elastomers or rubber mixtures. Silicas for rubber applications are generally prepared by a process in which the precipitation takes place at temperatures of from 60 to 95° C. and at a pH of from 7 to 10, see for example EP 0 901 986 A1.

It is an object of the present invention to provide novel, readily dispersible precipitated silicas which can be incorporated in elastomer mixtures and which improve their properties.

Surprisingly, it has now been found that precipitation at a constant AV can give novel silicas which can be incorporated particularly effectively into elastomer mixtures and improve their properties.

The present invention therefore provides readily dispersible precipitated silicas characterized by:
CTAB surface area 100-160 m$^2$/g, the preferred ranges being 100-150 m$^2$/g, 100-135 m$^2$/g, and 100-120 m$^2$/g
BET surface area 100-190 m$^2$/g, the preferred range being 100-170 m$^2$/g, 100-160 m$^2$/g, 100-140 m$^2$/g, and 110-135 m$^2$/g,
DBP value 180-300 g/(100 g), preferred range 200-280 g/(100 g),
Sears value V$_2$ 15-28 ml/(5 g), the preferred range being 20-28 ml/(5 g) and 22 to 28 ml/(5 g) and particularly 25-28 ml/(5 g),
Moisture level 4-8%.

The precipitated silicas of the invention may moreover preferably have one or more of the following physico-chemical parameters:
Ratio of Sears value V$_2$ to BET surface area 0.140-0.280 ml/(5 m$^2$), the preferred ranges being 0.150-0.280 ml/(5 m$^2$), 0.170-0.280 ml/(5 m$^2$), 0.180-0.280 ml/(5 m$^2$), and particularly preferably 0.190-0.280 ml/(5 m$^2$) and 0.190-0.250 ml/(5 m$^2$),
Ratio of BET to CTAB 0.9-1.2, preferably 1-1.15,
Primary particle diameter 10-80 nm.

By way of example, the primary particle diameter may be determined by evaluating transmission electron micrographs (TEMs) (R. H. Lange, J. Bloedorn: "Das Elektronenmikroskop, TEM+REM" [The electron microscope, TEM+SEM] Thieme Verlag, Stuttgart, N.Y. (1981)).

In a first preferred embodiment, the precipitated silicas of the invention have a DBP value of 200-250 g/(100 g), and in a second preferred embodiment they have a DBP value of 250-280 g/(100 g).

The precipitated silicas of the invention have not only a high absolute number of silanol groups (Sears value V$_2$), but also, when comparison is made with prior-art precipitated silicas, a markedly increased ratio of the Sears value V$_2$ to the BET surface area. This means that the precipitated silicas of the invention in particular have a very high number of silanol groups based on the total surface area.

The precipitated silicas of the invention have not only an increased number of silanol groups but also low microporosity, i.e. a very low ratio of BET to CTAB.

The combination of the features mentioned, in particular the high ratio of Sears value V$_2$ to BET, gives the precipitated silicas of the invention excellent suitability as reinforcing fillers for elastomers. These precipitated silicas of the invention have increased rubber activity, and exhibit very good dispersion behavior and a low vulcanization time.

The present invention further provides a process which can be used to prepare the precipitated silicas of the invention with
CTAB surface area 100-160 m$^2$/g, the preferred ranges being 100-150 m$^2$/g, 100-135 m$^2$/g, and 100-120 m$^2$/g,
BET surface area 100-190 m$^2$/g, the preferred range being 100-170 m$^2$/g, 100-160 m$^2$/g, 100-140 m$^2$/g, and 110-135 m$^2$/g,
DBP value 180-300 g/(100 g), preferred range 200-280 g/(100 g),
Sears value V$_2$ 15-28 ml/(5 g), the preferred range being 20-28 ml/(5 g) and 22 to 28 ml/(5 g) and particularly 25-28 ml/(5 g),
Moisture level 4-8%,
and, where appropriate, with one or more of the following physico-chemical parameters
Ratio of Sears value V$_2$ to BET surface area 0.140-0.280 ml/(5 m$^2$), the preferred ranges being 0.150-0.280 ml/(5 m$^2$), 0.170-0.280 ml/(5 m$^2$), 0.180-0.280 ml/(5 m$^2$), and particularly preferably 0.190-0.280 ml/(5 m$^2$) and 0.190-0.250 ml/(5 m$^2$),
Ratio of BET to CTAB 0.9-1.2, preferably 1-1.15,
primary particle diameter 10-80 nm,
which comprises first
a) taking an aqueous solution of an alkali metal silicate or alkaline earth metal silicate and/or of an organic and/or inorganic base with an alkali value from 7 to 30 as initial charge,
b) metering water glass and an acidifier simultaneously into this initial charge at from 55 to 95° C., with stirring, for from 10 to 120 minutes, preferably from 10 to 60 minutes, particularly preferably from 60 to 100 minutes, in such a way that during the precipitation the AV value remains constant at from 7 to 30, c) using an acidifier to acidify to pH of from about 2.5 to 6, and d) filtering, washing, drying and, where appropriate, pelletizing.

The initial charge may amount to about 20, 30, 40, 50, 60, 70, 80, or 90% of the final volume for the precipitation. The basic compounds for the initial charge are in particular selected from the group of the alkali metal hydroxides, alkaline earth metal hydroxides, alkali metal carbonates, alkali metal hydrogencarbonates, and alkali metal silicates. Preference is given to the use of water glass and/or sodium hydroxide solution.

The constant alkali value in the initial charge and during step b) is in the range from 7 to 30, preferably from 10 to 30, and is particularly preferably from 15 to 25, and it is very particularly preferable for the AV to be held at a value of from 18 to 22.

Optionally, the feed during step b) may be interrupted, the steps carried out then comprising b') stopping the feed for from 30 to 90 minutes while maintaining the temperature, and b") then, at the same temperature, for from 10 to 120 minutes, preferably from 10 to 60 minutes, simultaneously adding water glass and an acidifier in such a way that the AV remains constant during the precipitation.

Another addition of organic or inorganic salts may moreover optionally be incorporated during one or more of steps a) and/or b) and/or b') and/or b"). This addition may be carried out in solution or in solid form, in each case continuously over the period of addition of the water glass and of the acidifier, or may be batch addition. It is also possible for the salts to be dissolved in one or both of the components and then to be added simultaneously with these.

The inorganic salts preferably used are alkali metal salts or alkaline earth metal salts. In particular, use may be made of any of the combinations of the following ions:
$Li^+$, $Na^+$, $K^+$, $Rb^+$, $Be^{2+}$, $Mg^{2+}$, $Ca^{2+}$, $Sr^{2+}$, $Ba^{2+}$, $H^+$, $F^-$, $Cl^-$, $Br^-$, $I^-$, $SO_2^-$, $SO_4^{2-}$, $HSO_4^-$, $PO_3^{3-}$, $PO_4^{3-}$, $NO_3^-$, $NO_2^-$, $CO_3^{2-}$, $HCO_3^-$, $OH^-$, $TiO_3^{2-}$, $ZrO_3^{2-}$, $ZrO_4^{4-}$, $AlO_2^-$, $Al_2O_4^{2-}$, $BO_4^{3-}$.

Suitable organic salts are the salts of formic, acetic, or propionic acid. Cations which may be mentioned are the abovementioned alkali metal ions or alkaline earth metal ions. The concentration of these salts in the solution added may be from 0.01 to 5 mol/l. The inorganic salt preferably used is $Na_2SO_4$.

Besides water glass (sodium silicate solution), use may also be made of other silicates, such as potassium silicate or calcium silicate. Acidifiers which may be used, besides sulfuric acid, are HCl, $HNO_3$, $H_3PO_4$, or $CO_2$.

In step d), the precipitated silica is first filtered and then washed with water, and dried. The silica here is washed until the content of sodium sulfate is <4% by weight. The sodium sulfate content may be measured by the method known to the person skilled in the art, e.g. as described in EP 0 754 650 A1.

The filtration of the silicas of the invention and their drying for a long or short period are familiar to the person skilled in the art, and details may be found in the abovementioned documents, for example.

The silica precipitated is preferably dried in a pneumatic drier, spray drier, disk drier, belt drier, rotating-tube drier, flash drier, spin flash drier, or spray tower. These drying methods include operation using an atomizer, using a single- or twin-fluid nozzle, or using an integrated fluidized bed.

Where appropriate, after the drying process grinding may take place, and/or a roller compactor may be used for pelletizing. After the drying step, the grinding, or the pelletization, the precipitated silica of the invention preferably has a particle shape with an average diameter above 15 μm, in particular above 80 μm, particularly preferably above 200 μm (determined ISO 2591-1, December 1988). The precipitated silicas of the invention particularly preferably take the form of a powder with an average diameter above 15 μm, or take the form of substantively round particles with an average diameter above 80 μm (microbeads), or take the form of pellets with an average diameter ≥1 mm.

The present invention also provides the use of a precipitated silica, with a

CTAB surface area 100-160 $m^2/g$, the preferred ranges being 100-150 $m^2/g$, 100-135 $m^2/g$, and 100-120 $m^2/g$, BET surface area 100-190 $m^2/g$, the preferred range being 100-170 $m^2/g$, 100-160 $m^2/g$, 100-140 $m^2/g$, and 110-135 $m^2/g$, DBP value 180-300 g/(100 g), preferred range 200-280 g/(100 g)

Sears value $V_2$ 15-28 ml/(5 g), the preferred range being 20-28 ml/(5 g) and 22 to 28 ml/(5 g) and particularly 25-28 ml/(5 g), Moisture level 4-8% and also, where appropriate, with one or more of the following physico-chemical parameters Ratio of Sears value $V_2$ to BET surface area 0.140-0.280 ml/(5 $m^2$), the preferred ranges being 0.150-0.280 ml/(5 $m^2$), 0.170-0.280 ml/(5 $m^2$), 0.180-0.280 ml/(5 $m^2$), and particularly preferably 0.190-0.280 ml/(5 $m^2$) and 0.190-0.250 ml/(5 $m^2$), Ratio of BET to CTAB 0.9-1.2, preferably 1-1.15 primary particle diameter 10-80 nm for preparing elastomer mixtures, vulcanizable rubber mixtures, and/or other vulcanizates.

The invention also provides elastomer mixtures, vulcanizable rubber mixtures, and/or other vulcanizates which comprise the silica of the invention, examples being moldings, such as pneumatic tires, tire treads, cable sheathing, hoses, drive belts, conveyor belts, roller coverings, tires, shoe soles, ring seals, and damping elements.

The silicas of the invention may also be used in any of the application sectors which usually use silicas, e.g. in battery separators, as antiblocking agent, as matting agent in inks and paints, as carrier for agricultural products and for feeds, in coatings, in printing inks, in fire-extinguisher powders, in plastics, in the non-impact printing sector, in paper pulp, or in the personal care sector, or in specialty applications.

Use in the non-impact printing sector, for example in inkjet printing, is use of the silicas of the invention in printing inks for thickening or for preventing splashing and offset, paper, as filler or coating pigment, blueprint paper, heat-sensitive paper, thermal sublimation for preventing strike-through of printing inks, for improvement in contrast and image background uniformity, and for improvement in dot definition and color brilliance.

Use in the personal care sector is use of the silicas of the invention as filler or thickener, e.g. in the pharmaceutical sector or the body-care sector.

The silica of the invention may optionally be modified with silanes or organosilanes of the formulae I to III $$[SiR^1{}_n(OR)_r(Alk)_m(Ar)_p]_q[B] \quad (I),$$

$$SiR^1{}_n(OR)_{3-n}(Alkyl) \quad (II)$$

or $$SiR^1{}_n(OR)_{3-n}(Alkenyl) \quad (III),$$

where

B is —SCN, —SH, —Cl, —NH$_2$, —OC(O)CHCH$_2$, —OC(O)C(CH$_3$)CH$_2$ (if q=1), or —S$_w$— (if q=2), B being chemically bonded to Alk, R and R$^1$ are an aliphatic, olefinic, aromatic, or arylaromatic radical having 2-30 carbon atoms, optionally with substitution by the following groups: the hydroxyl, amino, alcoholate, cyanide, thiocyanide, halo, sulfonic acid, sulfonic ester, thiol, benzoic acid, benzoic ester, carboxylic acid, carboxylic ester, acrylate, methacrylate, or organosilane radical, where the meaning or substitution of R and R$^1$ may be identical or different, n is 0, 1, or 2, Alk is a bivalent unbranched or branched hydrocarbon radical having from 1 to 6 carbon atoms, m is 0 or 1, Ar is an aryl radical having from 6 to 12 carbon atoms, preferably 6 carbon atoms, which may have substitution by the following groups: the hydroxyl, amino, alcoholate, cyanide, thiocyanide, halo, sulfonic acid, sulfonic ester, thiol, benzoic acid, benzoic ester, carboxylic acid, carboxylic ester, or organosilane radical, p is 0 or 1, with the proviso that p and n are not simultaneously 0, q is 1 or 2, w is a number from 2 to 8, r is 1, 2, or 3, with the proviso that r+n+m+p=4, Alkyl is a monovalent unbranched or branched saturated hydrocarbon radical having from 1 to 20 carbon atoms, preferably from 2 to 8 carbon atoms, Alkenyl is a monovalent unbranched or branched unsaturated hydrocarbon radical having from 2 to 20 carbon atoms, preferably from 2 to 8 carbon atoms.

The silica of the invention may also be modified with organosilicon compounds of the composition SiR$^2{}_{4-n}$X$_n$ (where n=1, 2, 3, 4), [SiR$^2{}_x$X$_y$O]$_z$ (where 0≤x≤2; 0≤y≤2; 3≤z≤10, where x+y=2), [SiR$^2{}_x$X$_y$N]$_z$ (where 0≤x≤2; 0≤y≤2; 3≤z≤10, where x+y=2), SiR$^2{}_n$X$_m$OSiR$^2{}_o$X$_p$ (where 0≤n≤3; 0≤m≤3; 0≤o≤3; 0≤p≤3, where n+m=3, o+p=3), SiR$^2{}_n$X$_m$NSiR$^2{}_o$X$_p$ (where 0≤n≤3; 0≤m≤3; 0≤o≤3; 0≤p≤3, where n+m=3, o+p=3), SiR$^2{}_n$X$_m$[SiR$^2{}_x$X$_y$O]$_z$SR$^2{}_o$X$_p$ (where 0≤n≤3; 0≤m≤3; 0≤x≤2; 0' y≤2; 0≤o≤3; 0≤p≤3; 1≤z≤10000, where n+m=3, x+y=2, o+p=3). These compounds may be linear, cyclic, or branched, silane, silazane, or siloxane compounds. R$^2$ may be substituted and/or unsubstituted alkyl and/or aryl radicals, in each case having 1-20 carbon atoms, which may have substitution by functional groups, for example by the hydroxyl group, by the amino group, by polyethers, such as ethylene oxide and/or propylene oxide, or by halide groups, such as fluoride. R$^2$ may also include groups such as alkoxy, alkenyl, alkynyl, and aryl groups, and sulfur-containing groups. X may be reactive groups, such as the silanol, amino, thiol, halogen, alkoxy, and alkenyl groups, and a hydrogen radical.

Preference is given to linear polysiloxanes of composition SiR$^2{}_n$X$_m$[SiR$^2{}_x$R$_y$O]$_z$SiR$^2{}_o$X$_p$ (where 0≤n≤3; 0≤m≤3; 0≤x≤2; 0≤y≤2; 0≤o≤3; 0≤p≤3; 1≤z≤10000, where n+m=3; x+y=2; o+p=3), R$^2$ preferably being methyl.

Particular preference is given to polysiloxanes of composition SiR$^2{}_n$X$_m$[SiR$^2{}_x$X$_y$O]$_z$SiR$^2{}_o$X$_p$ (where 0≤n≤3; 0≤m≤1; 0≤x≤2; 0≤y≤2; 0≤o≤3; 0≤p≤1; 1≤z≤1000, where n+m=3, x+y=2, o+p=3), R$^2$ preferably being methyl.

The modification of the optionally pelletized, unpelletized, ground, and/or unground precipitated silica with one or more of the organosilanes mentioned may take place in mixtures of from 0.5 to 50 parts, based on 100 parts of precipitated silica, in particular from 1 to 15 parts, based on 100 parts of precipitated silica, where the reaction between precipitated silica and organosilane may be carried out during preparation of the mixture (in situ) or externally via spray application and subsequent heat-conditioning of the mixture, via mixing of the organosilane and the silica suspension with subsequent drying and heat-conditioning (e.g. as in DE 34 37 473 and DE 196 09 619), or by the process described in DE 196 09 619 or DE-C 40 04 781.

Suitable organosilicon compounds are in principle any of the bifunctional silanes which firstly can brine about coupling to the filler containing silanol groups secondly can bring about coupling to the polymer. Amounts usually used as the organosilicon compounds are from 1 to 10% by weight, based on the total amount of precipitated silica.

Examples of these organosilicon compounds are: bis(3-triethoxysilylpropyl)tetrasulfane, bis(3-triethoxysilylpropyl)disulfane, vinyltrimethoxysilane, vinyltriethoxysilane, 3-mercaptopropyltrimethoxysilane, 3-mercaptopropyltriethoxysilane, 3-aminopropyltrimethoxysilane, 3-aminopropyltriethoxysilane. Other organosilicon compounds have been described in WO 99/09036, EP 1 108 231, DE 101 37 809, DE 101 63 945, DE 102 23 658.

In one preferred embodiment of the invention, bis(3-triethoxysilylpropyl)tetrasulfane may be used as silane.

The silica of the invention may be incorporated as reinforcing filler in elastomer mixtures, tires, or vulcanizable rubber mixtures, in amounts of from 5 to 200 parts, based on 100 parts of rubber, in the form of powder, beads, or pellets, either with silane modification or else without silane modification.

For the purposes of the present invention, rubber mixtures and elastomer mixtures are regarded as equivalent.

The silanol groups on the silica surface function in rubber mixtures as possible chemical reaction partners for a coupling reagent. By way of example, this is a bifunctional silane, such as bis(3-triethoxysilylpropyl)tetrasulfane, which permits the linkage of the silica to the rubber matrix. The maximum number of silanol groups therefore achieves high probability of coupling between silica and the coupling reagent, and thus high probability of linkage of the silica to the rubber matrix, the final result of this being higher reinforcing potential. The Sears value $V_2$ is a dimension allowing description of the number of silanol groups in the silica, while the BET surface area of a silica describes its specific surface area, which has a major effect on the processing behavior of a compounded material, and on its other properties after vulcanization. However, the data relating to the absolute number of silanol groups are not themselves sufficient for adequate characterization of a precipitated silica, because precipitated silicas with a high surface area generally have a higher absolute number of silanol groups than precipitated silicas with a low surface area. The important factor is therefore the quotient calculated by dividing the Sears value $V_2$ by the BET. In this way it is possible to represent the reinforcement potential generated via the silanol groups per unit of specific surface area introduced.

The fillers in the elastomer mixtures or rubber mixtures may comprise not only mixtures comprising exclusively the silicas of the invention, with or without the abovementioned organosilanes but also one or more other fillers with relatively high or relatively low reinforcing capability.

The other fillers used may comprise the following materials:

Carbon blacks: the carbon blacks to be used here are prepared by the flame black process, furnace black process, or gas black process, and have BET surface areas of from 20 to 200 $m^2/g$, e.g. SAF, ISAF, HSAF, HAF, FEF, or GPF blacks. Where appropriate, the carbon blacks may also contain heteroatoms, e.g. silicon.

Fine-particle fumed silicas, e.g. prepared by flame hydrolysis of silicon halides. Where appropriate, the silicas may also be mixed oxides with other metal oxides, such as Al oxides, Mg oxides, Ca oxides, Ba oxides, Zn oxides, or titanium oxides.

Other commercially available silicas.

Synthetic silicates, such as aluminum silicate, or alkaline earth metal silicates, such as magnesium silicate or calcium silicate, with BET surface areas of from 20 to 400 $m^2/g$ and with primary particle diameters of from 10 to 400 nm.

Synthetic or natural aluminum oxides and synthetic or natural aluminum hydroxides.

Natural silicates, such as kaolin, and other naturally occurring silicon dioxide compounds.

Glass fiber and glass fiber products (mats, strands), or glass microbeads.

Starch and modified grades of starch.

Naturally occurring fillers, e.g. clays and siliceous chalk.

Here, as with the amounts used of the organosilanes, the mixing ratio depends on the property profile to be achieved in the finished rubber mixture. A conceivable ratio, also implemented here, between the silicas of the invention and the other abovementioned fillers (including a mixture) is 5-95%.

In one particularly preferred embodiment, from 10 to 150 parts by weight of silicas, composed entirely or to some extent of the silica of the invention, may be used to prepare the mixtures, where appropriate together with from 0 to 100 parts by weight of carbon black, use may also be made of from 1 to 10 parts by weight of an organosilicon compound, based in each case on 100 parts by weight of rubber.

Another important constituent of the rubber mixture, besides the silicas of the invention, the organosilanes, and other fillers, is the elastomers. Mention may be made here of elastomers, natural or synthetic, oil-extended or non-oil-extended, in the form of single polymer or blend with other rubbers, examples being natural rubbers, polybutadiene (BR), polyisoprene (IR), styrene/butadiene copolymers having styrene contents of from 1 to 60% by weight, preferably from 2 to 50% by weight (SBR), in particular prepared by means of the solution polymerization process, butyl rubbers, isobutylene-isoprene copolymers (IIR), butadiene-acrylonitrile copolymers having acrylonitrile contents of from 5 to 60% by weight, preferably from 10 to 50% by weight (NBR), partially or fully hydrogenated NBR rubber (HNBR), ethylene-propylene-diene copolymers (EPDM), or else a mixture of these rubbers.

The following additional rubbers may also be used for rubber mixtures with the rubbers mentioned:
carboxy rubbers, epoxy rubbers, trans-polypentenamers, halogenated butyl rubbers, 2-chlorobutadiene rubbers, ethylene-vinyl acetate copolymers, ethylene-propylene copolymers, and, where appropriate, also chemically derivatized natural rubber, and also modified natural rubbers.

By way of example, W. Hofmann, "Kautschuktechnologie" [Rubber technology], Genter Verlag, Stuttgart, 1980, describes preferred synthetic rubbers.

Anionically polymerized SSBR rubbers (solution SBRs) with a glass transition temperature above −50° C. are of particular interest for producing the tires of the invention, as are mixtures of these with diene rubbers.

The silicas of the invention, with or without silane, may be used in any of the applications of rubbers, for example moldings, tires, tire treads, conveyor belts, gaskets, drive belts, hoses, shoe soles, cable sheathing, roller coverings, damping elements, etc.

The incorporation of this silica and the preparation of the mixtures comprising this silica, take place in an internal mixer or on a roll mill, preferably at 80-200° C., in the manner conventional in the rubber industry. The form in which the silicas are used may be either powder, beads, or pellets. Again, there is no difference between the silicas of the invention and the known pale-color fillers.

The rubber vulcanizates of the invention may comprise the usual amounts of other rubber auxiliaries, such as reaction accelerators, antioxidants, heat stabilizers, light stabilizers, ozone stabilizers, processing aids, plasticizers, tackifiers, blowing agents, dyes, pigments, waxes, extenders, organic acids, retarders, metal oxides, and also activators, such as triethanolamine, polyethylene glycol, and hexanetriol. These compounds are known in the rubber industry.

The amounts which may be used of the rubber auxiliaries are those which are known, and depend, inter alia, on the intended use. Examples of usual amounts are from 0.1 to 50% by weight, based on the rubber used. Sulfur or sulfur-donor substances may be used as crosslinkers. The rubber mixtures of the invention may moreover comprise vulcanization accelerators. Examples of suitable primary accelerators are mercaptobenzothiazoles, sulfenamides, thiurames, and dithiocarbamates in amounts of from 0.5 to 3% by weight. Examples of coaccelerators are guanidines, thioureas, and thiocarbonates in amounts of from 0.5 to 5% by weight. The amounts of sulfur which may usually be used are from 0.1 to 10% by weight, preferably from 1 to 3% by weight, based on the rubber used.

The silicas of the invention may be used in rubbers which are crosslinkable using accelerators and/or sulfur, or else peroxidically crosslinkable.

The rubber mixtures of the invention may be vulcanized at temperatures of from 100 to 200° C., preferably from 130 to 180° C., where appropriate under a pressure of from 10 to 200 bar. Known mixing assemblies, such as roll mills, internal mixers, and mixing extruders, may be used for blending of the rubbers with the filler, where appropriate with rubber auxiliaries, and with the organosilicon compound.

The rubber mixtures of the invention are suitable for producing moldings, for example for producing pneumatic tires, tire treads for tires for summer, winter, or year-round use, car tires, tires for utility vehicles, motorcycle tires, tire carcass components, cable sheathing, hoses, drive belts, conveyor belts, roller coverings, shoe soles, gasket ring seals, and damping elements.

The silicas of the invention have the advantage of providing a higher level of reinforcement in the rubber vulcanizates, and thus improved abrasion resistance, due to the higher level of rubber activity, when comparison is made with an identical rubber mixture using silicas known hitherto. In addition, they exhibit very good dispersion properties, and also advantages in vulcanization time.

The rubber mixtures of the invention are particularly suitable for producing tire treads for car tires with low rolling resistance or with good suitability for winter conditions. The rubber mixtures of the invention are also suitable, without addition of organosilicon compounds, blended with a typical tire tread carbon black, for improving the cut & chip performance of tires on construction machinery, on agricultural machinery, or tires used in mining. (For definitions and further details see "New insights into the tear mechanism" and references cited therein, presented by Dr. W. Niederme-er at Tire Tech 2003 in Hamburg.)

The reaction conditions and the physico-chemical data for the precipitated silicas of the invention are determined using the following methods:

Determination of Moisture Level of Silicas

Based on ISO 787-2, this method is used to determine the volatile content (hereinafter termed moisture level for simplicity) of silica after drying for 2 hours at 105° C. This loss on drying is generally composed mainly of moisture.

Method 10 g of the silica in powder, bead, or pellet form are weighed out precisely to 0.1 mg into a dry glass weighing vessel with ground-glass lid (diameter 8 cm, height 3 cm) (specimen weight E). With the lid open, the specimen is dried for 2 h at 105±2° C. in a drying cabinet. The glass weighing vessel is then sealed, and cooled to room temperature in a desiccator cabinet, using silica gel as drying agent. The specimen is weighed to give the final weight A.

The moisture level in % is determined as ((E in g–A in g)*100%)/(E in g).

Determination of Modified Sears Value of Silicas

The modified Sears value (hereinafter termed Sears value $V_2$) can be determined by titrating silica with potassium hydroxide solution in the range from pH 6 to pH 9, and is a measure of the number of free hydroxy groups.

The following chemical reactions underlie the determination method, "Si"-OH being intended to symbolize a silanol group of the silica:

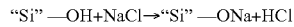

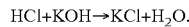

Method 10.00 g of a silica in powder, bead or pellet form, having a moisture level of 5±1%, are comminuted for 60 seconds, using an M 20 IKA universal mill (550 W; 20 000 rpm). Where appropriate, the moisture content of the starting substance has to be adjusted by drying at 105° C. in the drying cabinet or uniform moistening, with repeated comminution. 2.50 g of the silica thus treated are weighed out at room temperature into a 250 ml titration vessel and mixed with 60.0 ml of analytical grade methanol. After complete wetting of the specimen, 40.0 ml of deionized water are added, and the mixture is dispersed, using a T 25 UltraTurrax mixer (KV-18G mixing shaft, 18 mm diameter) for 30 seconds at a rotation rate of 18 000 rpm. The particles of specimen adhering to the edge of the vessel and to the stirrer are flushed into the suspension, using 100 ml of deionized water, and a water bath with thermostat is used to control the temperature of the mixture to 25° C. The pH tester (Knick 766 Calimatic pH meter with temperature sensor) and pH electrode (Schott N7680 combination electrode) are calibrated using buffer solutions (pH 7.00 and 9.00) at room temperature. Using the pH meter, the initial pH of the suspension is first measured at 25° C., and then, depending on the result, potassium hydroxide solution (0.1 mol/l) or hydrochloric acid solution (0.1 mol/l) is used to adjust the pH to 6.00. The consumption of KOH solution or HCl solution in ml required to reach pH 6.00 corresponds to $V_1'$.

20.0 ml of sodium chloride solution (250.00 g of analytical grade NaCl made up to 1 l using deionized water) are then metered in. The titration is then continued as far as pH 9.00, using 0.1 mol/l KOH. The consumption of KOH solution in ml required to reach pH 9.00 corresponds to $V_2'$.

The volumes $V_1'$ and $V_2'$ are first then normalized for a theoretical specimen weight of 1 g, and are then multiplied by 5, thus giving $V_1$ and the Sears value $V_2$ in the units ml/(5 g).

Determination of BET Surface Area

The specific nitrogen surface area (hereinafter termed BET surface area) of the silica in powder, bead, or pellet form is determined to ISO 5794-1/Annex D, using an AREA-meter (Ströhlein, JUWE).

CTAB Surface Area Determination

The method is based on the adsorption of CTAB (N-hexadecyl-N,N,N-trimethylammonium bromide) on the "external" surface of the silica, also termed the "rubber-active surface", and is based on ASTM3765 or NFT 45-007 (Section 5.12.1.3). CTAB is adsorbed in aqueous solution, with stirring and treatment with ultrasound. Excess, unadsorbed CTAB is determined by back-titration with NDSS (solution of the sodium salt of dioctyl sulfosuccinate, "Aerosol OT" solution), using a titroprocessor, the end point being given by maximum clouding of the solution, and determined using a phototrode. The temperature during all of the operations carried out is 23-25° C., in order to prevent CTAB from crystallizing out. The following equation underlies the back-titration reaction:

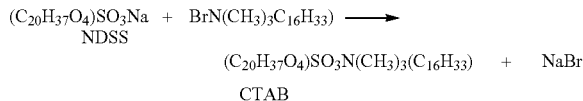

Equipment

METTLER Toledo DL 55 titroprocessor and METTLER Toledo DL 70 titroprocessor, in each case equipped with:

DG 111 pH electrode produced by Mettler, and DP 550 phototrode produced by Mettler 100 ml polypropylene titration beaker 150 ml glass titration vessel with lid Pressure-filtration equipment, capacity 100 ml Membrane filter composed of cellulose nitrate, pore size 0.1 μm, diameter 47 mm, e.g. Whatman (order no. 7181-004)

Reagents

The solutions of CTAB (0.015 mol/l in deionized water) and NDSS (0.00423 mol/l in deionized water) are purchased in ready-to-use form (Kraft, Duisburg: order no. 6056.4700 CTAB solution, 0.015 mol/l; order no. 6057.4700 NDSS solution, 0.00423 mol/l), stored at 25° C., and used within one month.

Method

Blind Titration

The consumption of NDSS solution for the titration of 5 ml of CTAB solution is to be tested once daily prior to each series of tests. For this, the phototrode is adjusted to 1000±20 mV (corresponding to 100% transparency) prior to starting the titration.

Exactly 5.00 ml of CTAB solution are pipetted into a titration beaker, and 50.0 ml of deionized water are added. The titration with NDSS solution uses the test method familiar to the person skilled in the art, with stirring, using the DL 55 titroprocessor until max. clouding of the solution has been reached. The consumption $V_1$ of NDSS solution is determined in ml. Three determinations are to be carried out for each titration.

Adsorption 10.0 g of the silica in powder, bead or pellet form, with a moisture content of 5±2% (the moisture content being adjusted, where appropriate, by drying at 105° C. in the drying cabinet or uniform moistening), are comminuted for 30 seconds, using a mill (Krups KM 75, item no. 2030-70). Exactly 500.0 mg of the comminuted specimen are transferred into a 150 ml titration vessel with magnetic stirrer bar, and exactly 100.0 ml of CTAB solution are metered in. The titration vessel is sealed with a lid, and the mixture is stirred for 15 minutes, using a magnetic stirrer. Hydrophobic silicas are stirred, using a T 25 UltraTurrax mixer (KV-18G mixer shaft, 18 mm diameter), at 18 000 rpm for a maximum of 1 min to give complete wetting. The titration vessel is screw-fastened to the DL 70 titroprocessor, and the pH of the suspension is adjusted to a value of 9±0.05, using KOH (0.1 mol/l). The suspension is exposed for 4 minutes to ultrasound, in the titration vessel, in an ultrasound bath (Sonorex RK 106 S from Bandelin, 35 KHz) at 25° C. This is followed immediately by filtration under pressure through a membrane filter, the nitrogen pressure being 1.2 bar. The first 5 ml of filtrate are discarded.

Titration 5.00 ml of the remaining filtrate are pipetted into a 100 ml titration beaker and made up to 50.00 ml, using deionized water. The titration beaker is screw-fastened to the DL 55 titroprocessor, and the mixture is titrated with NDSS solution, with stirring, until maximum clouding has been reached. The consumption $V_{II}$ of NDSS solution in ml is determined. Each clouding point is to be determined three times.

Calculation

The measured values $V_I$=consumption of NDSS solution in ml when the blind specimen is titrated $V_{II}$=consumption of NDSS solution in ml when the filtrate is used give:

$V_I/V_{II}$=amount of CTAB in the blind specimen/remaining amount of CTAB present in the filtrate specimen.

The amount N of adsorbed CTAB in g is therefore:

$N=((V_I-V_{II})*5.5\ g*5\ ml)/V_I*1000\ ml)$.

Because only 5 ml were titrated from 100 ml of filtrate, and 0.5 kg of silica of a defined moisture level was used, and the area required by 1 g of CTAB is $578435*10^{-1}$ m² and:

CTAB surface area (not corrected for water) in m²/g= $(N*20*578.435\ m^2/g)/(0.5\ g)$, and CTAB surface area (not corrected for water) in m²/g=$((V_I-V_{II})*636.2785\ m^2/g)/V_I$.

The CTAB surface area is based on the anhydrous silica, and the following correction is therefore made:

CTAB surface area in m²/g=(CTAB surface area (not corrected for water) in m²/g*100%)/(100%−moisture level in %).

Determination of DBP Absorption

DBP absorption (DBP number) is determined as follows by a method based on the standard DIN 53601, and is a measure of the absorbency of the precipitated silica:

Method 12.50 g of silica in powder or bead form with 0-10% moisture content (the moisture content being adjusted, where appropriate, by drying at 105° C. in the drying cabinet) are placed in the kneader chamber (item no. 279061) of the Brabender "E" Absorptometer (with no damping of the output filter of the torque sensor). In the case of pellets, the sieve fraction from 3.15 to 1 mm (Retsch stainless-steel sieve) is used (by using slight pressure from a plastics spatula to press the pellets through the 3.15 mm-pore-width sieve). While the material is constantly mixed (rotation rate of kneader paddles: 125 rpm), dibutyl phthalate is added dropwise at a rate of 4 ml/min at room temperature into the mixture by way of the "Brabender T 90/50 Dosimat". Incorporation by mixing is achieved with only low power consumption, and is followed by means of the digital display. Toward the end of the determination, the mixture becomes pasty, and this is indicated by a steep rise in the power consumption. When the display shows 600 digits (0.6 Nm torque), both the kneader and the DBP feed are switched off via an electrical contactor. The synchronous motor for the DBP supply has coupling to a digital meter, thus permitting read-off of DBP consumption in ml.

Evaluation

DBP absorption is stated in g/(100 g), and is calculated from the measured DBP consumption by using the following formula. The density of DBP at 20° C. is typically 1.047 g/ml.

DBP absorption in g/(100 g)=((DBP consumption in ml)*(DBP density in g/ml)*100)/(12.5 g).

Defined DBP absorption relates to the anhydrous, dried silica. If moist precipitated silicas are used, the value is to be corrected by means of the following correction table. The correction value, corresponding to the water content, is added to the DBP value determined experimentally; by way of example, an addition of 33 g/(100 g) for DBP absorption would be implied if the water content were 5.8%.

Correction Table for Dibutyl Phthalate Absorption—Anhydrous—

| % water | .% water | | | | |
|---|---|---|---|---|---|
| | .0 | .2 | .4 | .6 | .8 |
| 0 | 0 | 2 | 4 | 5 | 7 |
| 1 | 9 | 10 | 12 | 13 | 15 |
| 2 | 16 | 18 | 19 | 20 | 22 |
| 3 | 23 | 24 | 26 | 27 | 28 |
| 4 | 28 | 29 | 29 | 30 | 31 |
| 5 | 31 | 32 | 32 | 33 | 33 |
| 6 | 34 | 34 | 35 | 35 | 36 |
| 7 | 36 | 37 | 38 | 38 | 39 |
| 8 | 39 | 40 | 40 | 41 | 41 |
| 9 | 42 | 43 | 43 | 44 | 44 |
| 10 | 45 | 45 | 46 | 46 | 47 | pH Determination

The method, based on DIN EN ISO 787-9, serves for determination of the pH of an aqueous suspension of silicas at 20° C. To this end, an aqueous suspension is prepared from the specimen to be studied. After brief shaking of the suspension, its pH is determined by means of a previously calibrated pH meter.

Method

Prior to making the pH measurement, daily calibration of the pH tester (Knick 766 Calimatic pH meter with temperature sensor) and of the pH electrode (Schott N7680 combination electrode, is required, using the buffer solutions, at 20° C. The calibration function is to be selected in such a way that the two buffer solutions used include the expected pH of the specimen (buffer solutions having pH 4.00 and 7.00, pH 7.00 and 9.00, and, where appropriate, pH 7.00 and 12.00). If pellets are used, 20.0 g of silica are first comminuted for 20 s by means of a mill (Krups KM 75, item No. 2030-70).

5.00 g of silica in powder or bead form, with 5±1% moisture content (where appropriate, the moisture content being adjusted by drying at 105° C. in the drying cabinet or by uniform wetting prior to any comminution) are precisely weighed out to 0.01 g on a precision balance into a previously tared wide-necked glass flask. 95.0 ml of deionized water are added to the specimen. An automatic shaker (Gerhardt, LS10, 55 W, level 7) is then used to shake the suspension in the sealed vessel for a period of 5 minutes at room temperature. The pH is measured directly after shaking. To this end, the electrode is rinsed first with deionized water and then with a portion of the suspension, and then dipped into the suspension. A magnetic stirrer bar is then added to the suspension, and the pH measurement is made at a constant stirring rate with formation of slight vortex in the suspension. When the pH meter displays a constant value, the pH is read off from the display.

The method when hydrophobic silica is used is similar, but in that case 5.00 g of the specimen, after comminution where appropriate and with 5±1% moisture content, are weighed out precisely to 0.01 g on the precision balance into a previously tared wide-necked glass flask. 50.0 ml of analytical grade methanol and 50.0 ml of deionized water are added, and an automatic shaker (Gerhardt, LS10, 55 W, level 7) is then used to shake the suspension in the sealed vessel for a period of 5 minutes at room temperature. The pH is likewise measured with stirring, but after precisely 5 min.

Determination of Solids Content of Filter Cake

This method is used to determine the solids content of filter cake via removal of the volatile content at 105° C.
Method
100.00 g of the filter cake are weighed out into a dry, tared porcelain dish (diameter 20 cm) (specimen weight E). Where appropriate, the filter cake is comminuted, using a spatula, in order to obtain separate fragments of not more than 1 cm$^3$. The specimen is dried to constant weight at 105±2° C. in a drying cabinet. The specimen is then cooled to room temperature in a desiccator cabinet, using silica gel as drying agent. The material is weighed to determine the final weight A.

The solids content in % is determined as 100%−(((E in g−A in g)*100%)/(E in g)).

Determination of Electrical Conductivity

The electrical conductivity (C) of silicas is determined in aqueous suspension.
Method
If pellets are used, 20.0 g of silica are first comminuted by means of a mill (Krups, KM 75, item No. 2030-70) for 20 s. 4.00 g of silica in powder or bead form, with 5±1% moisture content (the moisture content being adjusted, where appropriate, by drying at 105° C. in the drying cabinet or uniform wetting prior to any comminution) are suspended in 50.0 ml of deionized water, and heated for 1 min to 100° C. The specimen cooled to 20° C. is made to precisely 100 ml and homogenized by rotary shaking.

The measurement cell of the LF 530 (WTW) conductivity tester is flushed with a small amount of specimen before the LTA01 measurement cell is dipped into the suspension. The value displayed corresponds to the conductivity at 20° C., because the TFK 530 external temperature sensor automatically compensates for the temperature. Both this temperature coefficient and the cell constant k are to be checked prior to each series of tests.

The calibration solution used comprises 0.01 mol/l potassium chloride solution (C at 20° C.=1278 µS/cm).

Determination of Solids Content of Precipitation Suspension

The solids content of the precipitation suspension is determined gravimetrically after filtration of the specimen.
Method
100.0 ml of the homogenized precipitation suspension ($V_{suspension}$) are measured out at room temperature with the aid of a measuring cylinder. The specimen is filtered off with suction by way of a round filter (Schleicher & Schuell 572) in a porcelain suction filter funnel, but not sucked dry, so as to avoid cracking of the filter cake. The filter cake is then washed with 100.0 ml of deionized water. The suction-filtration of the leached filter cake is then completed, and the filter cake is transferred into a tared porcelain dish and dried to constant weight at 105±2° C. in a drying cabinet. The weight of the dried silica ($m_{specimen}$) is determined.

The solids content is determined as:

solids content in g/l=($m_{specimen}$ g)/($V_{suspension}$ in l).

Determination of Alkali Value

The alkali value (AV) determined is the consumption in ml of hydrochloric acid (using a specimen volume of 50 ml, 50 ml of dist. water, and a hydrochloric acid concentration of 0.5 mol/l) during direct potentiometric titration of alkaline solutions or alkaline suspensions as far as pH 8.30. The result reveals the free alkali content of the solution or suspension.
Method
The pH device (Knick, Calimatic 766 pH meter with temperature sensor) and the pH electrode (Schott N7680 combination electrode) are calibrated at room temperature with the aid of two buffer solutions (pH=7.00 and pH=10.00). The combination electrode is dipped into the test solution or test suspension, the temperature of which has been controlled to 40° C., and which is composed of 50.0 ml of specimen and 50.0 ml of deionized water. Hydrochloric acid solution whose concentration is 0.5 mol/l is then added dropwise until a constant pH of 8.30 is obtained. Because the equilibrium between the silica and the free alkali content is established only slowly, a waiting time of 15 min is required before final read-off of the acid consumption. For the amounts and concentrations selected, the read-off of hydrochloric acid consumption in ml directly corresponds to the alkali value, which is a dimensionless quantity.

The following examples are intended to provide further illustration of the invention but not to limit its scope.

EXAMPLE 1

Preparation of Silicas

Example 1.1

1550 l of water and 141.4 kg of water glass (density 1.348 kg/l, 27.0% SiO$_2$, 8.05% Na$_2$O) form an initial charge in a reactor made from stainless steel with a propeller-stirrer system and jacket heating. 5.505 kg/min of the abovementioned water glass and about 0.65 kg/min of sulfuric acid (density 1.83 kg/l, 96% H$_2$SO$_4$) are then metered in with vigorous stirring at 92° C. over a period of 80 minutes. This metering of sulfuric acid is regulated in such a way that the alkali value prevailing in the reaction mixture is 20. The water glass addition is then stopped, and the addition of sulfuric acid is continued until a pH of 5.0 (measured at room temperature) has been achieved. The resultant suspension is filtered, using a membrane filter press, and the product is washed with water. The filter cake, with 21% solids content, is liquidized, using aqueous sulfuric acid and a shearing assembly. The silica feed with 18% solids content and with a pH of 4.0 is then spray-tower dried with addition of ammonia.

The resultant microbead product has a BET surface area of 123 $m^2/g$ and a CTAB surface area of 119 $m^2/g$.

Example 1.2

1550 l of water and 141.4 kg of water glass (density 1.348 kg/l, 27.0% $SiO_2$, 8.05% $Na_2O$) form an initial charge in a reactor made from stainless steel with a propeller-stirrer system and jacket heating. 5.505 kg/min of the abovementioned water glass and about 0.65 kg/min of sulfuric acid (density 1.83 kg/l, 96% $H_2SO_4$) are then metered in with vigorous stirring at 88.5° C. over a period of 80 minutes. This metering of sulfuric acid is regulated in such a way that the alkali value prevailing in the reaction mixture is 20. The water glass addition is then stopped, and the addition of sulfuric acid is continued until a pH of 4.5 (measured at room temperature) has been achieved. The resultant suspension is filtered, using a membrane filter press, and the product is washed with water. The filter cake, with 19% solids content, is liquidized, using aqueous sulfuric acid and a shearing assembly. The silica feed with 19% solids content and with a pH of 3.0 is then spray-tower dried with addition of ammonia.

The resultant microbead product has a BET surface area of 168 $m^2/g$ and a CTAB surface area of 148 $m^2/g$.

Example 1.3

1550 l of water and 141.4 kg of water glass (density 1.348 kg/l, 27.0% $SiO_2$, 8.05% $Na_2O$) form an initial charge in a reactor made from stainless steel with a propeller-stirrer system and jacket heating. 5.505 kg/min of the abovementioned water glass and about 0.65 kg/min of sulfuric acid (density 1.83 kg/l, 96% $H_2SO_4$) are then metered in with vigorous stirring at 93° C. over a period of 80 minutes. This metering of sulfuric acid is regulated in such a way that the alkali value prevailing in the reaction mixture is 20. The water glass addition is then stopped, and the addition of sulfuric acid is continued until a pH of 5.0 (measured at room temperature) has been achieved. The resultant suspension is filtered, using a membrane filter press, and the product is washed with water. The filter cake, with 21% solids content, is liquidized, using aqueous sulfuric acid and a shearing assembly. The silica feed with 1.8% solids content and with a pH of 4.0 is then spray-dried with addition of ammonia and roller-granulated.

The resultant granulated product has a BET surface area of 126 $m^2/g$ and a CTAB surface area of 118 $m^2/g$.

Example 1.4

1 550 l of water and 141.4 kg of water glass (density 1.348 kg/l, 27.0% $SiO_2$, 8.05% $Na_2O$) formed an initial charge in a stainless steel reactor with propeller-stirrer system and jacket heating.

5.505 kg/min of the abovementioned water glass and about 0.65 kg/min of sulfuric acid (density 1.83 kg/l, 96% $H_2SO_4$) are then added at 92° C. over a period of 100 minutes, with vigorous stirring. This sulfuric acid addition is regulated in such a way that the AV prevailing in the reaction mixture is 20. The addition of water glass is then stopped, and the supply of sulfuric acid is continued until a pH of 5.0 (measured at room temperature) has been reached.

The resultant suspension is filtered, using a membrane filter press, and washed with water. The filter cake, with 22% solids content, is liquidized, using aqueous sulfuric acid and a shearing assembly. The silica feed, with 19% solids content and with a pH of 3.8, is then spray-dried with ammonia feed and roller-granulated.

The resultant granular product has a BET surface area of 130 $m^2/g$ and a CTAB surface area of 113 $m^2/g$.

Example 1.5

1 550 l of water and 141.4 kg of water glass (density 1.348 kg/l, 27.0% $SiO_2$, 8.05% $Na_2O$) formed an initial charge in a stainless steel reactor with propeller-stirrer system and jacket heating.

5.505 kg/min of the abovementioned water glass and about 0.65 kg/min of sulfuric acid (density 1.83 kg/l, 96% $H_2SO_4$) are then added at 92.0° C. over a period of 100 minutes, with vigorous stirring. This sulfuric acid addition is regulated in such a way that the AV prevailing in the reaction mixture is 20. The addition of water glass is then stopped, and the supply of sulfuric acid is continued until a pH of 5.0 (measured at room temperature) has been reached.

The resultant suspension is filtered, using a membrane filter press, and washed with water. The filter cake, with 21% solids content, is liquidized, using aqueous sulfuric acid and a shearing assembly. The silica feed, with 19% solids content and with a pH of 4.0 is then spray-tower dried with ammonia feed.

The resultant microbead product has a BET surface area of 110 $m^2/g$ and a CTAB surface area of 108 $m^2/g$.

Example 1.6

1 550 l of water and 141.4 kg of water glass (density 1.348 kg/l, 27.0% $SiO_2$, 8.05% $Na_2O$) formed an initial charge in a stainless steel reactor with propeller-stirrer system and jacket heating.

5.505 kg/min of the abovementioned water glass and about 0.65 kg/min of sulfuric acid (density 1.83 kg/l, 96% $H_2SO_4$) are then added at 88.0° C. over a period of 100 minutes, with vigorous stirring. This sulfuric acid addition is regulated in such a way that the AV prevailing in the reaction mixture is 20. The addition of water glass is then stopped, and the supply of sulfuric acid is continued until a pH of 5.0 (measured at room temperature) has been reached.

The resultant suspension is filtered, using a membrane filter press, and washed with water. The filter cake, with 22% solids content, is liquidized, using aqueous sulfuric acid and a shearing assembly. The silica feed, with 20% solids content and with a pH of 3.0 is then spray-tower dried with ammonia feed.

The resultant microbead product has a BET surface area of 143 $m^2/g$ and a CTAB surface area of 131 $m^2/g$.

Further physico-chemical data for the abovementioned silicas are given in the following table.

| Silica from Example No. | BET [m²/g] | CTAB [m²/g] | DBP [g/(100 g)] | Moisture [%] | pH [—] | Conductivity [µS/cm] | Sears value V₂ [ml/(5 g)] | Sears value V₂/BET [ml/(5 m²)] |
|---|---|---|---|---|---|---|---|---|
| 1.1 | 123 | 119 | 272 | 4.8 | 5.6 | 610 | 24 | 0.195 |
| 1.2 | 168 | 148 | 265 | 5.5 | 6.0 | 700 | 26 | 0.155 |
| 1.3 | 126 | 118 | 207 | 5.1 | 5.1 | 810 | 22 | 0.175 |
| 1.4 | 130 | 113 | 204 | 5.2 | 6.2 | 720 | 22 | 0.169 |
| 1.5 | 110 | 108 | 271 | 5.1 | 5.5 | 930 | 25 | 0.227 |
| 1.6 | 143 | 131 | 258 | 4.8 | 5.7 | 580 | 26 | 0.182 |

EXAMPLE 2

Example 2.1

The precipitated silicas 1.1 and 1.3 of the invention from Example 1 were studied in an SBR emulsion rubber mixture. The silica Ultrasil VN2 GR from Degussa AG with a CTAB surface area of 125 m²/g was selected as prior art and reference.

The mixing specification used for the rubber mixtures is given in Table 2.1 below. The unit phr here means parts by weight, based on 100 parts of the untreated rubber used.

TABLE 2.1

|  | Reference | A | B |
|---|---|---|---|
| 1st stage |  |  |  |
| Buna SBR 1712 | 137.5 | 137.5 | 137.5 |
| Ultrasil VN2 GR | 50 | — | — |
| Silica as per Ex. 1.1 | — | 50 | — |
| Silica as per Ex. 1.3 | — | — | 50 |
| X50-S | 3 | 3 | 3 |
| ZnO | 3 | 2 | 3 |
| Stearic acid | 1 | 1 | 1 |
| Vulkanox 4020 | 2 | 2 | 2 |
| Protector G 3108 | 1.5 | 1.5 | 1.5 |
| 2nd stage |  |  |  |
| Stage 1 batch |  |  |  |
| 3rd stage |  |  |  |
| Stage 2 batch |  |  |  |
| Vulkacit D/C | 1.5 | 1.5 | 1.5 |
| Vulkacit CZ/EG | 1.5 | 1.5 | 1.5 |
| Sulfur | 2.2 | 2.2 | 2.2 |

Polymer Buna 1712 is an emulsion-polymerized SBR copolymer from Buna DOW Leuna with a styrene content of 23.5% by weight and with an oil content of 37.5 phr. X50-S is a 50/50 blend of Si 69 [bis(3-triethoxysilylpropyl)tetrasulfane] and carbon black obtainable from Degussa AG. Vulkanox 4020 is 6PPD from Bayer AG, and Protektor G 3108 is an ozone-protection wax from HB-Fuller GmbH. Vulkacit D/C (DPG) and Vulkacit CZ/EG (CBS) are commercially available products from Bayer AG.

The rubber mixtures are prepared in an internal mixer using the mixing instructions in Table 2.2. Table 2.3 gives the methods used for rubber testing. The mixtures are vulcanized at 160° C. for 18 minutes. Table 2.4 shows the results of testing on the vulcanized rubber.

TABLE 2.2

| Stage 1 | |
|---|---|
| Settings | |
| Mixing assembly | Werner & Pfleiderer 1.5 N |
| Rotation rate | 45 rpm |
| Friction | 1:1.11 |
| Ram pressure | 5.5 bar |
| Capacity | 1.6 l |
| Fill level | 0.73 |
| Chamber temp. | 70° C. |
| Mixing procedure | |
| 0-1 min | Polymer |
| 1-2 min | 1st stage constituents |
| 2 min | Purging |
| 2-3 min | Mixing, aerating |
| 3-4 min | Mixing at 70 rpm, aerating |
| 4-5 min | Mixing at 75 rpm, discharging |
| Aging | 24 h at room temperature |
| Stage 2 | |
| Settings | |
| Mixing assembly | as in stage 1 except: |
| Rotation rate | 70 rpm |
| Fill level | 0.71 |
| Mixing procedure | |
| 0-1 min | stage 1 batch, plasticize |
| 1-3 min | maintain batch temperature 140-150° C. by varying rotation rate |
| 3 min | Discharge |
| Aging | 4 h at room temperature |
| Stage 3 | |
| Settings | |
| Mixing assembly | as in stage 1 except: |
| Rotation rate | 40 rpm |
| Chamber temp. | 50° C. |
| Fill level | 0.69 |
| Mixing procedure | |
| 0-2 min | stage 2 batch, stage 3 constituents |
| 2 min | discharge and form milled sheet on laboratory roll mill, (diameter 200 mm, length 450 mm, roll temperature 50° C.) homogenization: cut the material 3 times toward the left, 3 times toward the right; fold the material over 3 times with wide roll gap (3.5 mm) and 3 times with narrow roll gap (1 mm): peel milled sheet away |

TABLE 2.3

| Physical testing | Standard/conditions |
|---|---|
| Vulcameter testing, 160° C. | DIN 53529/3, ISO 6502 |
| Torque difference Dmax – Dmin [dNm] | |
| t10% and t90% [min] | |
| Ring tensile test, 23° C. | DIN 53504, ISO 37 |
| Stress values 100% and 500% [Mpa] | |
| Reinforcement factor: stress value 300%/100% [—] | |
| Elongation at break [%] | |
| Shore A hardness, 23° C. [—] | DIN 53 505 |
| Ball rebound [%], 0° C. and 60° C. | DIN EN ISO 8307 steel ball, 19 mm, 28 g |
| Dispersion coefficient [%] | see text |

The dispersion coefficient was determined using the surface topography inc. Medalia correction (A. Wehmeier, "Filler Dispersion Analysis by Topography Measurements" Technical Report TR 820, Degussa AG, Advanced Fillers and Pigments Division). The dispersion coefficient thus determined correlates directly at reliability level >0.95 with the optically determined dispersion coefficient, for example as determined by the Deutschen Institut für Kautschuktechnologie e.V. [Germany Institute for Rubber Technology], Hanover, Germany (H. Geisler, Bestimmung der Mischgute, presented at DIK Workshop, 27-28 Nov. 1997, Hanover, Germany).

TABLE 2.4

| | Reference | A | B |
|---|---|---|---|
| Data for untreated mixture | | | |
| Dmax – Dmin | 11.5 | 11.8 | 11.6 |
| t10% | 4.9 | 4.6 | 4.6 |
| t90% | 9.8 | 9.6 | 9.5 |
| Vulcanizate data | | | |
| 100% stress | 1.0 | 1.0 | 1.0 |
| 300% stress | 9.1 | 9.9 | 10.3 |
| 300%/100% stress | 9.1 | 9.9 | 10.3 |
| Elongation at break | 530 | 500 | 520 |
| Shore A hardness | 51 | 51 | 51 |
| Ball rebound 0° C. | 22.1 | 21.2 | 21.3 |
| Ball rebound 60° C. | 71.0 | 70.4 | 70.3 |
| Dispersion coefficient | 98 | 99 | 97 |

As can be seen from the data in Table 2.4, with the mixtures A and B the silicas of the invention have a lower vulcanization time t90% than the reference 20 mixture. In addition to the lower vulcanization time, advantages are to be found in particular in a higher 500% stress value and the increased reinforcement factor. The ball rebound values at 0 and 60° C. are comparable, and no shortcomings in the hysteresis behavior of the mixtures are therefore to be expected. The dispersion of the silicas of the invention is very good.

Example 2.2

The precipitated silica 1.2 of the invention from example 1 was studied in an SSBR/BR rubber mixture. The prior art and reference selected was the silica Ultrasil 3370 GR from Degussa AG with a CTAB surface area of 160 m²/g. The mixture used represents a model mixing specification for a car tire tread mixture.

The mixing specification used for the rubber mixtures is given in Table 2.5 below. The unit phr here means 15 parts by weight, based on 100 parts of the unprocessed rubber used.

TABLE 2.5

| | Reference | C |
|---|---|---|
| 1st Stage | | |
| Buna VSL 5025-1 | 96 | 96 |
| Buna CB 24 | 30 | 30 |
| Ultrasil 3370 GR | 80 | — |
| Silica of Ex. 1.2 | — | 80 |
| X50-S | 12.8 | 12.8 |
| ZnO | 2 | 2 |
| Stearic acid | 2 | 2 |
| Naftolen ZD | 10 | 10 |
| Vulkanox 4020 | 1.5 | 1.5 |
| Protektor G 3108 | 1 | 1 |
| 2nd Stage | | |
| Stage 1 batch | | |
| 3rd Stage | | |
| Stage 2 batch | | |
| Vulkacit D/C | 2.0 | 2.0 |
| Vulkacit CZ/EG | 1.5 | 1.5 |
| Perkazit TBZTD | 0.2 | 0.2 |
| Sulfur | 1.5 | 1.5 |

The polymer VSL 5025-1 is a solution-polymerized SBR copolymer from Bayer AG with a styrene content of 25% by weight and a butadiene content of 75% by weight. The copolymer comprises 37.5 phr of oil and has a Mooney viscosity (ML 1+4/100° C.) of 50±4. The polymer Buna CB 24 is a cis-1,4-polybutadiene (neodymium type), from Bayer AG with cis-1,4 content of at least 97% and a Mooney viscosity of 44±5. X50 S is a 50/50 blend of Si 69 [bis(3-triethoxysilyl-propyl)tetrasulfane] and carbon black obtainable from Degussa AG. The aromatic oil used comprises Naftolen ZD from Chemetall. Vulkanox 4020 is a 6PPD from Bayer AG, and Protektor G 3108 is an ozone-protection wax from HB-Fuller GmbH. Vulkacit D/C (DPG) and Vulkacit CZ/EG (CBS) are commercially available products from Bayer AG. Perkazit TBZTD is obtainable from Akzo Chemie GmbH. The rubber mixtures are prepared in an internal mixture, using the mixing specification in Table 2.6. In addition to the methods indicated in Table 2.3 for rubber testing, the methods given in Table 2.7 were used. The mixtures were vulcanized at 165° C. for 15 minutes. Table 2.8 shows the results of testing on the vulcanized rubber.

TABLE 2.6

| Stage 1 | |
|---|---|
| Settings | |
| Mixing assembly | Werner & Pfleiderer 1.5 N |
| Rotation rate | 70 rpm |
| Friction | 1:1.11 |
| Ram pressure | 5.5 bar |
| Capacity | 1.6 l |
| Fill level | 0.73 |
| Chamber temp. | 70° C. |
| Mixing procedure | |
| 0-1 min | Buna VSL 5025-1 + Buna CB 24 |
| 1-3 min | 1/2 of filler, X50-S |
| 3-4 min | 1/2 of filler, remaining stage 1 constituents |
| 4 min | Purging |
| 4-5 min | Mixing and discharge |
| Aging | 24 h at room temperature |

TABLE 2.6-continued

| Stage 2 | |
| --- | --- |
| Settings | |
| Mixing assembly | as in stage 1 except: |
| Rotation rate | 80 rpm |
| Chamber temp. | 80° C. |
| Fill level | 0.70 |
| Mixing procedure | |
| 0-2 min | Plasticize stage 1 batch |
| 2-5 min | Maintain batch temperature at 150° C. by varying rotation rate |
| 5 min | Discharge |
| Aging | 4 h at room temperature |
| Stage 3 | |
| Settings | |
| Mixing assembly | as in stage 1 except |
| Rotation rate | 40 rpm |
| Chamber temp. | 50° C. |
| Fill level | 0.69 |
| Mixing procedure | |
| 0-2 min | Stage 2 batch, stage 3 constituents |
| 2 min | Discharge and form milled sheet on laboratory mixing rolls, (diameter 200 mm, length 450 mm, roll temperature 50° C.) Homogenize: Cut the material 3 times toward the left, 3 times toward the right Fold the material over 5 times with narrow roll gap (1 mm) and 5 times with wide roll gap (3.5 mm) and peel milled sheet away |

TABLE 2.7

| Physical testing | Standard/conditions |
| --- | --- |
| Vulcameter testing, 165° C. Torque difference Dmax – Dmin [dNm] t10% and t90% [min] | DIN 53529/3, ISO 6502 |
| Viscoelastic properties, 0 and 60° C., 16 Hz, initial force 50 N and amplitude force 25 N Test value recorded after 2 min of test time, i.e. 2 min of conditioning Complex modulus E* [MPa] Loss factor tan δ [—] | DIN 53 513, ISO 2856 |

TABLE 2.8

| | Reference | C |
| --- | --- | --- |
| Unprocessed mixture data | | |
| Dmax – Dmin | 18.6 | 18.5 |
| t10% | 1.5 | 1.5 |
| t90% | 6.3 | 6.1 |
| Vulcanizate data | | |
| Stress value 100% | 2.8 | 2.8 |
| Stress value 300% | 13.4 | 14.7 |
| Stress value 300%/100% | 4.8 | 5.3 |
| Elongation at break | 370 | 330 |
| Shore A hardness | 66 | 66 |
| Ball rebound 0° C. | 15.3 | 15.2 |
| Ball rebound 60° C. | 61.4 | 61.6 |
| E* (0° C.) | 23.4 | 31.8 |
| E* (60° C.) | 8.8 | 9.0 |
| tan δ (0° C.) | 0.360 | 0.441 |
| tan δ (60° C.) | 0.129 | 0.110 |
| Dispersion coefficient | 95 | 99 |

As is seen from the data in Table 2.8, the advantages also found in example 2.1 are confirmed in the vulcanization kinetics and a higher level of reinforcement for the mixture C, using the silica of the invention. In addition, advantages are found in the hysteresis behavior of the mixture C. There is an increase in the loss factor tan δ (0° C.), indicating improved wet skid performance, and there is a decrease in tan δ (60° C.), indicating reduced rolling resistance. The dispersion quality of the silicas of the invention is moreover exceptionally high, with resultant advantages in road abrasion.

What is claimed is:

1. A precipitated silica which has the following physical and chemical properties:

| | |
| --- | --- |
| CTAB surface area | 100-160 m$^2$/g |
| BET surface area | 100-190 m$^2$/g |
| DBP value | 180-300 g/(100 g) |
| Sears value V$_2$ | 15-28 ml/(5 g) |
| Moisture level | 4-8% |
| Ratio of Sears value V$_2$ to BET surface area | 0.150 to 0.280 ml/(5 m$^2$), | and
which has a primary particle diameter of 10-80 nm.

2. The precipitate silica as claimed in claim 1, wherein the BET surface area ranges from 100 to 170 m$^2$/g.

3. The precipitated silica as claimed in claim 1, wherein the CTAB surface area ranges from 100 to 150 m$^2$/g.

4. The precipitated silica as claimed in claim 1, wherein the Sears value V$_2$ ranges from 20 to 28 ml/(5 g).

5. The precipitated silica as claimed in claim 1, wherein the Sears value V$_2$ ranges from 22 to 28 ml/(5 g).

6. The precipitated silica as claimed in claim 1, wherein the DBP value ranges from 200 to 250 g/(100 g).

7. The precipitated silica as claimed in claim 1, wherein the DBP value ranges from 250 to 280 g/(100 g).

8. The precipitated silica as claimed in claim 1, wherein the ratio of Sears value V$_2$ to the BET surface area ranges from 0.170 to 0.280 ml/(5 m$^2$).

9. The precipitated silica as claimed in claim 1, wherein the BET/CTAB ratio ranges from 0.9 to 1.2.

10. The precipitated silica claimed in claim 1, wherein the surface of the precipitated silica is modified with organosilanes of the formulae I to III $$[SiR^1{}_n(OR)_r(Alk)_m(Ar)_p]_q[B] \qquad (I),$$

$$SiR^1{}_n(OR)_{3-n}(Alkyl) \qquad (II),$$

or $$SiR^1{}_n(OR)_{3-n}(Alkenyl) \qquad (III),$$

where

B is —SCN, —SH, —Cl, —NH$_2$, —OC(O)CHCH$_2$, —OC(O)C(CH$_3$)CH$_2$ (if q=1), or —S$_w$— (if q=2), B being chemically bonded to Alk, R and R$^1$, which are identical or different, are each an aliphatic, olefinic, aromatic, or arylaromatic radical having 2-30 carbon atoms, optionally substituted by at least one of the following groups: hydroxyl, amino, alcoholate, cyanide, thiocyanide, halo, sulfonic acid, sulfonic ester, thiol, benzoic acid, benzoic ester, carboxylic acid, carboxylic ester, acrylate, methacrylate, or organosilane;

n is 0, 1, or 2;

Alk is a bivalent unbranched or branched hydrocarbon radical having from 1 to 6 carbon atoms;

m is 0 or 1;

Ar is an aryl radical having from 6 to 12 carbon atoms, which may be substituted by one of the following groups: hydroxyl, amino, alcoholate, cyanide, thiocyanide, halo, sulfonic acid, sulfonic ester, thiol, benzoic acid, benzoic ester, carboxylic acid, carboxylic ester, acrylate, methacrylate or organosilane radical;

p is 0 or 1, with the proviso that p and n are not simultaneously 0;

q is 1 or 2;

w is a number from 2 to 8;

r is 1, 2, or 3, with the proviso that r+n+m+p=4;

Alkyl is a monovalent unbranched or branched saturated hydrocarbon radical having from 1 to 20 carbon atoms, Alkenyl is a monovalent unbranched or branched unsaturated hydrocarbon radical having from 2 to 20 carbon atoms.

11. The precipitated silica as claimed in claim 1, wherein the surface of the precipitated silica is modified with organosilicon compounds whose composition is $SiR^2_{4-n}X_n$ (where n=1, 2, 3, 4), $[SiR^2_xX_yO]_z$ (where $0 \leq x \leq 2$; $0 \leq y \leq 2$; $3 \leq z \leq 10$, where x+y=2), $[SiR^2_xX_yN]_z$ (where $0 \leq x \leq 2$; $0 \leq y \leq 2$; $3 \leq z \leq 10$, where x+y=2), $SiR^2_nX_mOSiR^2_oX_p$ (where $0 \leq n \leq 3$; $0 \leq m \leq 3$; $0 \leq o \leq 3$; $0 \leq p \leq 3$, where n+m=3, o+p=3), $SiR^2_nX_mNSiR^2_oX_p$ (where $0 \leq n \leq 3$; $0 \leq m \leq 3$; $0 \leq o \leq 3$; $0 \leq p \leq 3$, where n+m=3, o+p=3), and/or $SiR^2_nX_m[SiR^2_xX_yO]_zSiR^2_oX_p$ (where $0 \leq n \leq 3$; $0 \leq m \leq 3$; $0 \leq x \leq 2$; $0 \leq y \leq 2$; $0 \leq o \leq 3$; $0 \leq p \leq 3$; $1 \leq z \leq 10,000$, where n+m=3, x+y=2, o+p=3) where $R^2$ is alkyl and/or aryl radicals, substituted and/or unsubstituted, having from 1 to 20 carbon atoms, and/or is alkoxy and/or alkenyl and/or alkynyl groups, and/or is sulfur-containing groups, X is a silanol, amino, thiol, halogen, alkoxy, alkenyl and/or hydrogen radical.

12. A process for preparing the silicas as claimed in claim 10, which comprises modifying the precipitated silicas with organosilanes in mixtures of from 0.5 to 50 parts, based on 100 parts of precipitated silica, in particular from 1 to 15 parts, based on 100 parts of precipitated silica, where the reaction between precipitated silica and organosilane is carried out during the preparation of the mixture (in situ) or externally via spray application and subsequent heat-conditioning of the mixture, via mixing of the organosilane and the silica suspension with subsequent drying and heat-conditioning.

13. A vulcanizable rubber mixture or a vulcanizate whose filler component comprises the precipitated silica as claimed in claim 1 which has the following physical and chemical properties:

| | |
|---|---|
| CTAB surface area | 100-160 m²/g |
| BET surface area | 100-190 m²/g |
| DBP value | 180-300 g/(100 g) |
| Sears value $V_2$ | 15-28 ml/(5 g) |
| Moisture level | 4-8% |
| Ratio of Sears value $V_2$ to BET surface area | 0.150 to 0.280 ml/(5 m²). |

14. A process for preparing the silicas as claimed in claim 11, which comprises modifying the precipitated silicas with organosilanes in mixtures of from 0.5 to 50 parts, based on 100 parts of precipitated silica, in particular from 1 to 15 parts, based on 100 parts of precipitated silica, where the reaction between precipitated silica and organosilane is carried out during the preparation of the mixture (in situ) or externally via spray application and subsequent heat-conditioning of the mixture, via mixing of the organosilane and the silica suspension with subsequent drying and heat-conditioning.

15. A method of preparing an elastomer mixture, a vulcanizable rubber mixture, and/or another vulcanizate, comprising:

incorporating the precipitated silica of claim 1 into an elastomer mixture, a vulcanizable rubber mixture, and/or another vulcanizate elastomer mixture.

16. A battery separator, an antiblocking agent, a matting agent for inks and paints, a carrier for agricultural products and for feeds, a coating material, a printing ink, a fire-extinguisher powder, a plastic, in the non-impact printing sector, a paper pulp, or an article in the personal care sector, prepared by the presence of the precipitated silica of claim 1 as a component of the material from which the article is prepared.

17. The precipitated silica as claimed in claim 1, wherein the ratio of Sears value $V_2$ to the BET surface area ranges from 0.180 to 0.280 ml/(5 m²).

18. The precipitated silica as claimed in claim 1, wherein the ratio of Sears value $V_2$ to the BET surface area ranges from 0.190 to 0.280 ml/(5 m²).

19. The precipitated silica as claimed in claim 1, wherein the ratio of Sears value $V_2$ to the BET surface area ranges from 0.190 to 0.250 ml/(5 m²).

20. The precipitated silica as claimed in claim 1, wherein the Sears value $V_2$ ranges from 26 to 28 ml/(5 g).

\* \* \* \* \*